(12) United States Patent
Axelgaard

(10) Patent No.: US 9,089,684 B2
(45) Date of Patent: Jul. 28, 2015

(54) DUAL-SIDED CURRENT CONTROLLING ELECTRODE

(75) Inventor: Jens Axelgaard, Fallbrook, CA (US)

(73) Assignee: Axelgaard Manufacturing Company, Ltd., Fallbrook, CA (US)

( * ) Notice: Subject to any disclaimer, the term of this patent is extended or adjusted under 35 U.S.C. 154(b) by 259 days.

(21) Appl. No.: 13/371,739

(22) Filed: Feb. 13, 2012

(65) Prior Publication Data

US 2013/0211488 A1 Aug. 15, 2013

(51) Int. Cl.
*A61N 1/00* (2006.01)
*A61N 1/04* (2006.01)
*A61N 1/18* (2006.01)

(52) U.S. Cl.
CPC .......... *A61N 1/0452* (2013.01); *A61N 1/0456* (2013.01); *A61N 1/18* (2013.01)

(58) Field of Classification Search
CPC ............ A61N 1/00; A61N 1/02; A61N 1/04; A61N 1/18; A61N 1/40
See application file for complete search history.

(56) References Cited

U.S. PATENT DOCUMENTS

| | | |
|---|---|---|
| 4,736,752 A | 4/1988 | Munck et al. |
| 5,038,796 A | 8/1991 | Axelgaard et al. |
| 5,447,526 A | 9/1995 | Karsdon |
| 5,904,712 A | 5/1999 | Axelgaard |
| 6,745,082 B2 | 6/2004 | Axelgaard |
| 8,265,763 B2 | 9/2012 | Fahey |
| 8,320,988 B2 | 11/2012 | Axelgaard |
| 8,326,438 B2 | 12/2012 | Ayal et al. |
| 2011/0301683 A1 | 12/2011 | Axelgaard |

*Primary Examiner* — Christopher D Koharski
*Assistant Examiner* — Elizabeth K So
(74) *Attorney, Agent, or Firm* — Hackler Daghighian & Martino

(57) ABSTRACT

A field controlling electrode for providing transcutaneous nerve and/or muscle stimulation to a user's body includes a conductive flexible member having a top side and a bottom side. An electrically driven master electrode, in combination with the conductive flexible member, is provided for generating a current distribution in the conductive flexible member; and an electrically undriven slave electrode disposed in a spaced apart relationship with the master electrode is provided, for focusing or controlling the generated current distribution over an area of a user's body.

23 Claims, 3 Drawing Sheets

DUAL-SIDED CURRENT CONTROLLING ELECTRODE

The present invention generally relates to electrodes and, more particularly, electrodes suitable for transcutaneous nerve and/or muscle stimulation. Nerve and muscle cells are excitable because they are able to discharge action potentials and, accordingly, electrical stimulation of nerve and muscle membranes can evoke such action potential. In order for an action potential to be evoked, the stimulus intensity and pulse duration must be sufficient to pass a threshold. In this regard, muscle membranes require longer pulse durations due to their higher capacitance.

Thus, in order to meet this threshold, transcutaneous electrodes must not only be properly placed on the skin, but coupled thereto in order to provide sufficient current density to a particular cross-sectional body area. This is a very important factor in controlling the reaction of biological tissue to stimulation. As a rule, the greater the current density, the greater the resulting reaction on the tissue.

Earlier electrodes, such as set forth in U.S. Pat. No. 4,736,752, teach the control of current density across an electrode through the use of a conductive ink design area.

As hereinabove noted, electrodes must provide an even electrical coupling to a patient's skin over an entire surface of the electrode to effect proper interfacing. Because of the curvaceous nature of the human body, it is apparent that medical electrodes for use thereon must be flexible not only for confirmation with a patient's skin contours, but also to accommodate relative movement of the patient's skin.

Electrode placement is another factor that influences current density and, accordingly, tissue response. This is due to the fact that the impedance of skin, bone, and adipose tissue vary, and, accordingly, placement of electrodes over these tissues will have significant effect on current flow in the surrounding tissues. In addition, orientation of the electrodes can also significantly affect the response of underlying tissue. For example, muscle tissue is nearly four times more conductive in the longitudinal direction of their fibers than in the transverse direction.

In order to provide uniform electrical coupling, heretofore developed electrodes have utilized conductive fabrics and foils in combination with a conductive adhesive in order to uniformly couple electrical signals to and/or from an electrical lead wire, or connector. A number of electrodes have provided impedance compensation for directing electrical pulses from the lead wire uniformly throughout an electrode, such as, for example, U.S. Pat. No. 5,038,796 entitled, ELECTRICAL STIMULATION ELECTRODE WITH IMPEDANCE COMPENSATION, to Axelgaard. This patent teaches the use of an electrical shunt interconnected with the lead wire for causing more uniform resistance between equally spaced apart points in the electrode.

Without this shunt, many prior art electrodes have compromised the flexibility of the electrode in order to provide adequate current densities over the entire contact area of the electrode. These electrodes typically have utilized a metallic mesh, or foil, to provide conductivity and utilize a conductive gel between the electrode and the patient's skin in order to accommodate the movement therebetween. Contact between the lead wire and the metallic mesh, or foil, is typically a point contact. Because of this, electrode contacts to medical electrodes have typically been made on a top side thereof, that is, a side opposite a side of the electrode having a conductive adhesive thereon for application to a patient.

The present invention is directed to an electrode system which features control of current density utilizing multiple electrodes and/or shunt systems.

SUMMARY OF THE INVENTION

A field controlling electrode in accordance with the present invention for providing transcutaneous nerve and/or muscle stimulation generally includes a conductive flexible member having a top side and a bottom side.

An electrically driven master electrode is provided for generating a current distribution in the conductive flexible member and an electrically undriven slave electrode is disposed in a spaced apart relationship with the master electrode for focusing or controlling the generated current distribution.

Preferably, the master electrode is disposed on the conductive flexible member top side and a slave electrode is disposed on the conductive member bottom side. In addition, at least one of the master electrode and slave electrode may be a grid, preferably a conductive ink pattern.

In one embodiment of the present invention, the master and slave electrode have different planar shapes and in yet another embodiment of the present invention, multiple slave electrodes are provided. Multiple slave electrodes may be of differing sizes and/or shape.

For both identification of the electrode and obscuring construction of the electrode, an opaque non-conductive sheet may be disposed over the conductive flexible member top side and master electrode thereby enabling visualization only of the slave electrode, or electrodes, including the shape and/or placement thereof.

In addition, in order to further control the current distribution, the slave electrode may include a graded conductive ink pattern with varying line width and distance between lines of the pattern.

Further, an electrode shunt in electrical connection with both or either of the lead and master electrode may be provided to further enhance and control current distribution generated in the conductive flexible member.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
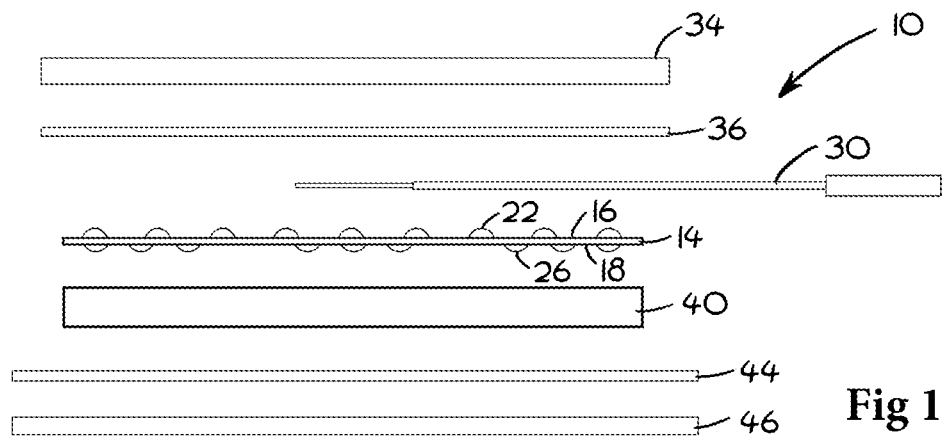
FIG. 1 is an exploded cross sectional view of a field controlling electrode in accordance with the present invention generally showing a conductive flexible member with an electrically driven master electrode disposed on the top side of the flexible member and electrically undriven slave electrode disposed on a bottom side of the flexible member.

With reference to FIG. 1, there is shown a field controlling electrode 10, in accordance with the present invention which generally includes a conductive flexible member 14 having a top side 16 and a bottom side 18.

As shown in FIG. 1, an electrically driven master electrode 22 is disposed on the conductive flexible member for generating a current distribution in the conductive flexible member 14.

An electrically undriven slave electrode 26 is disposed in a spaced apart relationship with the master electrode 22 for focusing or controlling the generated current distribution over an area of a user's body (not shown). In this instance, the undriven slave electrode 26 is disposed on the bottom side 18 of the flexible member 14. The master electrode 22 is connected via a lead 30 to external electrical apparatus (not shown).

A non-conductive flexible sheet 34 is disposed over the conductive flexible member 14 top side 16, master electrode 22, and lead 30 and adhered thereto by an adhesive layer 36.

It should be appreciated that any suitable master electrode 22 or slave electrode 26 may be utilized; however, preferably each of the master electrode 22 and slave electrode 26 is in the form of a grid, which comprises a conductive ink pattern. Such ink patterns are disclosed in U.S. Pat. No. 4,736,752, which is incorporated herewith in its entirety for the purpose of teaching the use of conductive ink design. The conductive flexible member may be formed from carbon and PVC or any other suitable material.

A suitable conductive hydrogel adhesive 40 is utilized for adhering the electrode 10 to a patient's skin (not shown).

A plastic carrier 46 along with a silicone coating 44 for easy release may be provided in order to prevent inadvertent and/or premature adhesion to a patient (not shown) or other object to the hydrogel 40 with the carrier 46 being removed prior to application of the electrode 10 to the patient (not shown).

Figure 2:
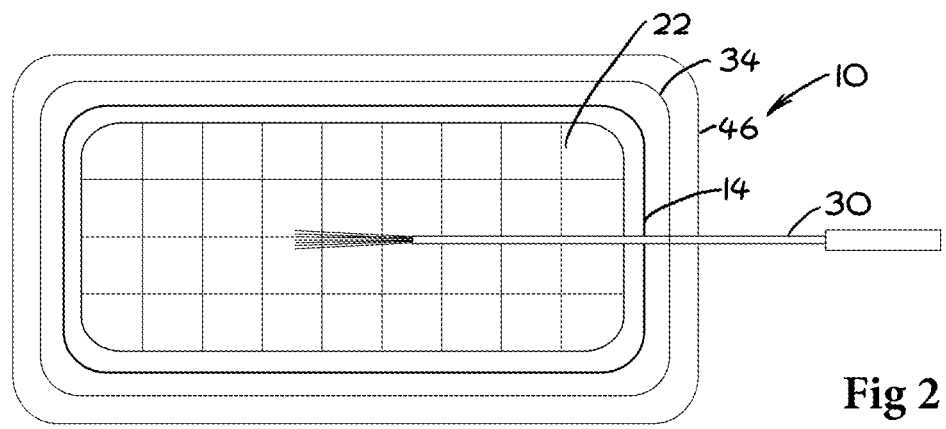
FIG. 2 is a plan view of the top side of the field controlling electrode shown in FIG. 1 showing the driven master electrode as being formed by a conductive ink pattern.
Figure 3:
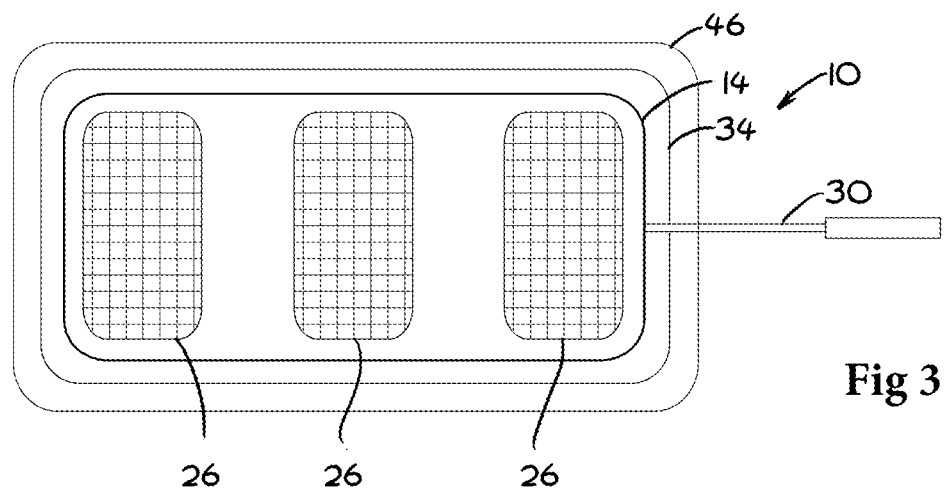
FIG. 3 is a bottom plane view of an electrode in accordance with the present invention illustrating the use of multiple slave electrodes.

With reference to FIGS. 2 and 3, top and bottom views of the electrode 10 are shown respectively. This embodiment illustrates not only that the master electrode 22 and slave electrode 26 have different planar shapes, but further multiple slave electrodes 26, in this case three, may be utilized in order to focus or control the generated current distribution in the conductive flexible member 14 by the master electrode 22.

Figure 4:
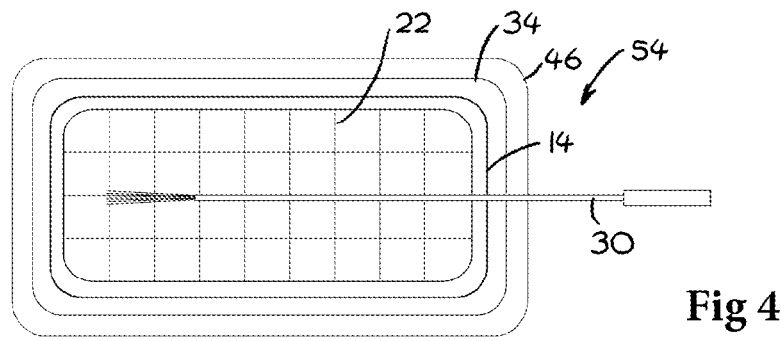
FIG. 4 is a view of an electrode similar to that shown in FIG. 2 with a different placement of a lead wire.
Figure 5:
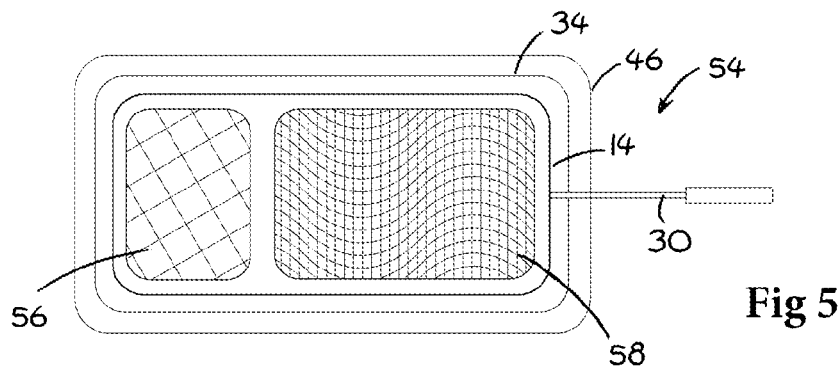
FIG. 5 is a bottom view of an electrode in accordance with the present invention illustrating multiple slave electrodes each having different conductive ink patterns with different planar shapes.

An alternative embodiment electrode 54 is illustrated in FIGS. 4 and 5 with common reference characters representing identical or similar elements as shown in FIGS. 1-3 describing the electrode 10.

In this field controlling electrode 54, with the top and bottom side respectively being shown in FIGS. 4 and 5, two slave electrodes 56, 58 are provided illustrating various arrays of grid patterns suitable for use for providing transcutaneous nerve and/or muscle stimulation to a user's body (not shown).

Figure 6:
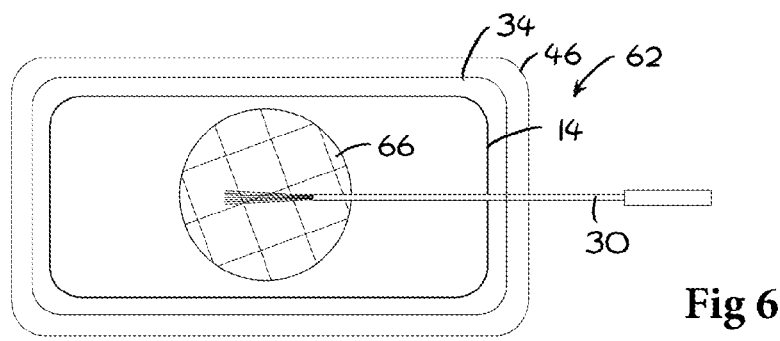
FIG. 6 is a top view of another embodiment of the present invention illustrating a circular electrically driven master electrode.
Figure 7:
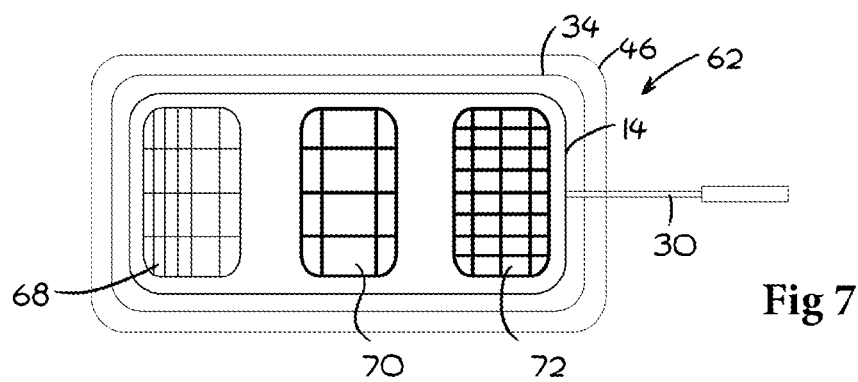
FIG. 7 illustrates a bottom view of yet another embodiment of the present invention illustrating multiple undriven slave electrodes having varying line widths and distance between lines of an ink pattern of the electrodes.

Another embodiment of a field controlling electrode 62, in accordance with the present invention, is illustrated in FIGS. 6 and 7, with FIG. 6 showing a top side and FIG. 7 showing a bottom side with common reference characters hereinabove described in conjunction with the electrodes 10 and 54.

In the case of electrode 62, the electrically driven master electrode 66 has a circular shape and three slave electrodes 68, 70, 72 are provided. The electrode 62 illustrates slave electrodes 68, 70, 72 having graded conductive ink patterns with varying line width and distance between lines of the pattern useful for focusing or controlling the generated current distribution in the flexible member 14 and the user's body (not shown) by the electrically driven master electrode 66.

Figure 8:
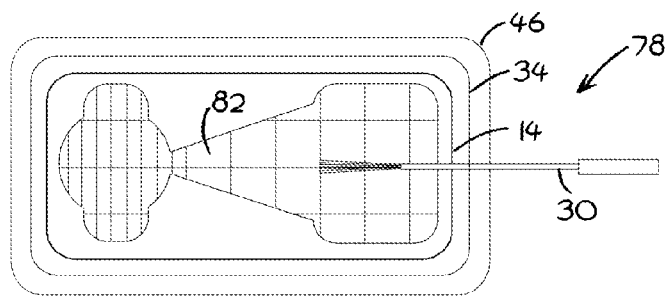
FIG. 8 is a top view of still another embodiment of the present invention illustrating various electrically driven master electrode shapes.
Figure 9:
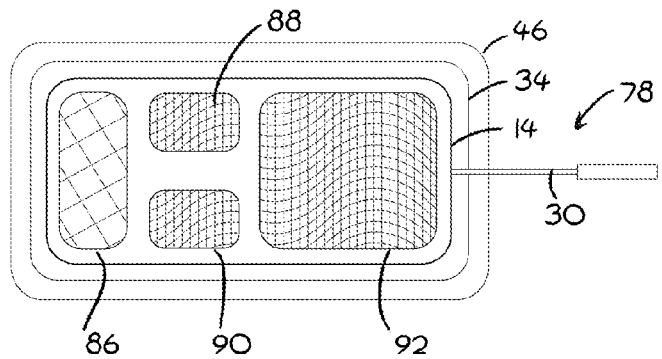
FIG. 9 is a plan view of the bottom of an electrode illustrating additional variation and placement of multiple undriven slave electrodes.

Turning now to FIGS. 8 and 9, there is shown yet another embodiment of a field controlling electrode 78 showing a master electrode 82 incorporating various grid designs and a planar shape and, as shown in FIG. 9, four slave electrodes 86, 88, 90, 92 with various planar shapes in grid configurations. This electrode 78 may be useful for stimulating the muscles proximal to a user's knee (not shown).

Figure 10:
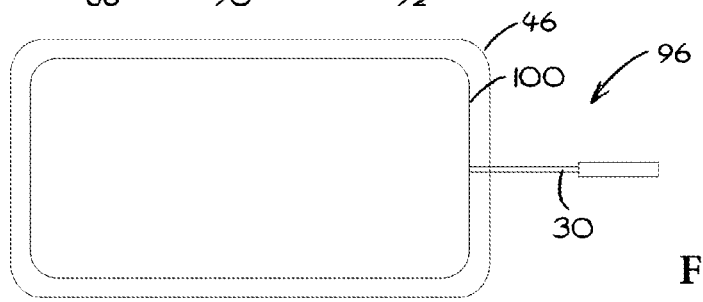
FIG. 10 is a plan view of an electrode top utilizing an opaque non-conductive sheet disposed over a conductive flexible member top side.

With reference to FIG. 10, an electrode 96 in accordance with the present invention may include an opaque non-conductive sheet 100 disposed over a conductive flexible member top side and master electrode, not seen in FIG. 10 to enable visualization only of a slave electrode (not shown in FIG. 10). In this manner, construction of the electrode is concealed yet the electrode is identifiable by the number and shape of slave electrodes 26, 56,58,68,70, 72, 86, 88, 90, and 92. This visualization enables proper selection of the electrode by the user with the slave electrodes 26, 56, 58, 68, 70, 72, 86, 88, 90, and 92 facilitating proper placement of the electrode 10, 54, 62, 78 on an area (not shown) of a user's body (not shown).

Figure 11:
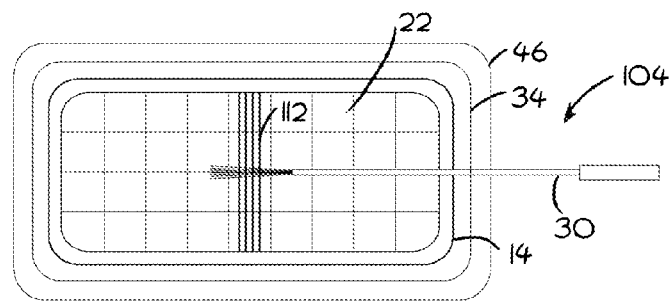
FIG. 11 is a plan view of an electrode top illustrating transverse placement of a shunt.
Figure 12:
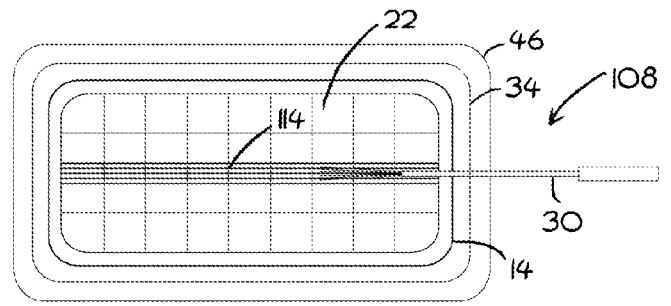
FIG. 12 is a plan view of an electrode top illustrating longitudinal placement of a shunt.

As shown in FIGS. 11 and 12, respectively, electrodes 104 and 108 illustrate the use of an electric shunt 112, 114, which may be in electrical communication with both or either of the lead 30, grid 22, and flexible member 14. The common reference numerals in FIGS. 11 and 12 represent identical or substantially similar elements as hereinabove discussed.

Various positions of the shunt of various sizes, or a plurality of shunts (not shown), may be utilized in various positions in order to further control current distribution that is generated in the conductive flexible member 14 by the master electrode 22. FIG. 11 represents a transverse placement of a shunt 112 and FIG. 12 illustrates a longitudinal placement of a shunt 114 with respect to the lead 30. The shunt may be of any suitable type such as a conductive pattern or discrete wires. The figures are merely representative of the shunt placement and the invention is not limited thereto. The shunt in combination with the dual-sided electrode provides greater current distribution than heretofore possible.

Although there has been hereinabove described a specific dual-sided current controlling electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A field controlling electrode for providing transcutaneous nerve and/or muscle stimulation to a user's body, said field controlling electrode comprising:
    a substantially flat conductive flexible member having a top side and a bottom side;
    a substantially flat electrically driven master electrode, in combination with said conductive flexible member, for generating a current distribution in said conductive flexible member; and
    a substantially flat electrically undriven slave electrode is disposed in a spaced apart relationship with said master electrode and in combination with said conductive flexible member, for focusing the generated current distribution over an area of a user's body;
    wherein the master electrode is disposed on the conductive flexible member top side and the slave electrode is disposed on the conductive flexible member bottom side, and
    wherein a lead is in direct electrical communication with the master electrode and not in direct electrical communication with the slave electrode, wherein the lead is for connecting the field controlling electrode to external electrical equipment.

2. The field controlling electrode according to claim 1 further comprising an electric shunt, in electrical communication with at least one of the lead and master electrode, for controlling current distribution generated in said conductive flexible member.

3. The field controlling electrode according to claim 2 wherein the shunt is disposed transverse to the lead.

4. The field controlling electrode according to claim 2 wherein the shunt is disposed longitudinally to the lead.

5. The field controlling electrode according to claim 1 wherein at least one of the master electrode and slave electrode is a grid.

6. The field controlling electrode according to claim 5 wherein said grid comprises a conductive ink pattern.

7. The field controlling electrode according to claim 1 wherein the master and slave electrode have different planar shapes.

8. The field controlling electrode according to claim 1 further comprising multiple slave electrodes.

9. The field controlling electrode according to claim 8 wherein the multiple slave electrode are of differing sizes and/or shape.

10. The field controlling electrode according to claim 9 wherein the master electrode is disposed on the conductive flexible member top side and the slave electrode is disposed on the conductive flexible member bottom side.

11. The field controlling electrode according to claim 10 further comprising a lead, in electrical communication with the master electrode, for connecting the electrode to external electrical equipment and an electric shunt, in electrical communication with at least one of the lead and master electrode, for controlling current distribution generated in said conductive flexible member.

12. The field controlling electrode according to claim 11 wherein the shunt is disposed transverse to the lead.

13. The field controlling electrode according to claim 11 wherein the shunt is disposed longitudinally to the lead.

14. The field controlling electrode according to claim 10 wherein at least one of the master and slave electrodes comprises a conductive ink pattern.

15. The field controlling electrode according to claim 10 wherein both the master and slave electrodes comprise conductive ink patterns.

16. The field controlling electrode according to claim 15 wherein the master and slave electrodes have different planar shapes.

17. The field controlling electrode according to claim 10 further comprising an opaque non-conductive sheet disposed over the conductive flexible member top side and master electrode thereby enabling visualization only of the slave electrode.

18. The field controlling electrode according to claim 1 further comprising an opaque non-conductive sheet disposed over the conductive flexible member top side and master electrode thereby enabling visualization only of the slave electrode.

19. The field controlling electrode according to claim 1 wherein the slave electrode comprises a graded conductive ink pattern having varying line width and/or distance between lines of the pattern.

20. A substantially flat field controlling electrode for providing transcutaneous nerve and/or muscle stimulation to a user's body, the field controlling electrode comprising:
    a conductive flexible member having a top side and a bottom side;
    an electrically driven master electrode disposed on the top side of the conductive flexible member for generating a current distribution in the conductive flexible member;
    an electrically undriven slave electrode is disposed in a spaced apart relationship with the master electrode on the bottom side of the conductive flexible member for focusing the generated current distribution over an area of a user's body; and
    a lead in electrical communication with the master electrode, wherein the lead is for connecting the field controlling electrode to external electrical equipment.

21. The field controlling electrode of claim 20, including an electric shunt in electrical communication with the lead and master electrode for controlling current distribution generated in said conductive flexible member.

22. The field controlling electrode of claim 20, further comprising an opaque non-conductive sheet disposed over the conductive flexible member top side and master electrode, the opaque non-conductive sheet including an image of the slave electrode thereby enabling visualization of the slave electrode during placement on the area of the user's body.

23. The field controlling electrode of claim 20, wherein the master and slave electrode have different planar shapes.

* * * * *